United States Patent [19]

Glick et al.

[11] Patent Number: 5,620,720
[45] Date of Patent: Apr. 15, 1997

[54] CAST MOLDING OF INTRAOCULAR LENSES

[75] Inventors: Robert E. Glick, Lake Forest; Jim Deacon, Capistrano Beach; Bruce W. Kent, San Dimas, all of Calif.

[73] Assignee: Allergan, Waco, Tex.

[21] Appl. No.: 346,974

[22] Filed: Nov. 29, 1994

[51] Int. Cl.⁶ ..................................................... B29D 11/00
[52] U.S. Cl. ........................ 425/408; 249/53 R; 249/117; 249/160; 249/168; 425/412; 425/808
[58] Field of Search ................................. 249/53 R, 117, 249/134, 160, 168; 425/215, 408, 412, 808

[56] References Cited

U.S. PATENT DOCUMENTS

| | | | |
|---|---|---|---|
| 1,577,132 | 3/1926 | Lawton | 249/168 |
| 1,653,396 | 12/1927 | Edwards | 249/168 |
| 3,605,195 | 9/1971 | Campbell . | |
| 3,915,609 | 10/1975 | Robinson | 425/174.6 |
| 4,095,772 | 6/1978 | Weber . | |
| 4,121,896 | 10/1978 | Shepherd . | |
| 4,197,266 | 4/1980 | Clark et al. . | |
| 4,201,289 | 5/1980 | Mack et al. | 249/117 |
| 4,208,364 | 6/1980 | Shepherd . | |
| 4,209,289 | 6/1980 | Newcomb et al. | 249/117 |
| 4,211,384 | 7/1980 | Bourset et al. . | |
| 4,265,850 | 5/1981 | Coulon et al. | 249/168 |
| 4,285,890 | 8/1981 | Mizutani et al. | 264/1.1 |
| 4,390,482 | 6/1983 | Feurer . | |
| 4,469,646 | 9/1984 | Rawlings . | |
| 4,534,723 | 8/1985 | Dillon et al. . | |
| 4,761,069 | 8/1988 | Truong et al. . | |
| 4,815,690 | 3/1989 | Shepherd | 249/82 |
| 4,865,779 | 9/1989 | Ihn et al. . | |
| 4,955,580 | 9/1990 | Seden et al. . | |
| 5,087,015 | 2/1992 | Galley . | |
| 5,147,397 | 9/1992 | Christ et al. . | |
| 5,185,107 | 2/1993 | Blake . | |
| 5,192,318 | 3/1993 | Schneider et al. . | |
| 5,236,970 | 8/1993 | Christ et al. . | |
| 5,255,888 | 10/1993 | Workman | 249/48 |

FOREIGN PATENT DOCUMENTS

| | | |
|---|---|---|
| 227365 | 7/1987 | European Pat. Off. . |
| 0367513 | 5/1990 | European Pat. Off. . |
| 484015 | 5/1992 | European Pat. Off. . |
| 2219413 | 12/1989 | United Kingdom . |
| 2235408 | 8/1990 | United Kingdom . |
| 2230730 | 10/1990 | United Kingdom . |
| 2235407 | 3/1991 | United Kingdom . |
| 9004512 | 5/1990 | WIPO . |
| WO93/04848 | 3/1993 | WIPO . |

Primary Examiner—James P. Mackey
Attorney, Agent, or Firm—Donald E. Stout

[57] ABSTRACT

The invention provides a disposable plastic mold assembly for an intraocular lens or the optic body thereof, which is inexpensive, less labor intensive than prior art intraocular lens molding techniques, and produces an intraocular lens having smooth, polished edges which require little or no post-mold finishing work. Numerous innovative features of the invention include an edge design which assures a seal between the male and female molds to thereby minimize flash during the cast molding operation, and the provision of a way to pre-align the male and female molds during assembly, consisting of an interference fitting relationship between the male and female molds. An additional feature is a way to maintain contact between the male and female molds during casting, which particularly involves the provision of a negative draft angle on the inner surface of the female mold's outer wall, or, alternatively, texturing which is applied to that inner surface so that it engages the outer edge at the top of the male mold during assembly. Yet another important feature of the invention is a structure for achieving axial and rotational orientation to produce lens edge geometries without unwanted steps on the lens edge. The alignment is achieved with interlocking steps on the male and female molds. The interlocking elements may be pins or annular elements.

18 Claims, 3 Drawing Sheets

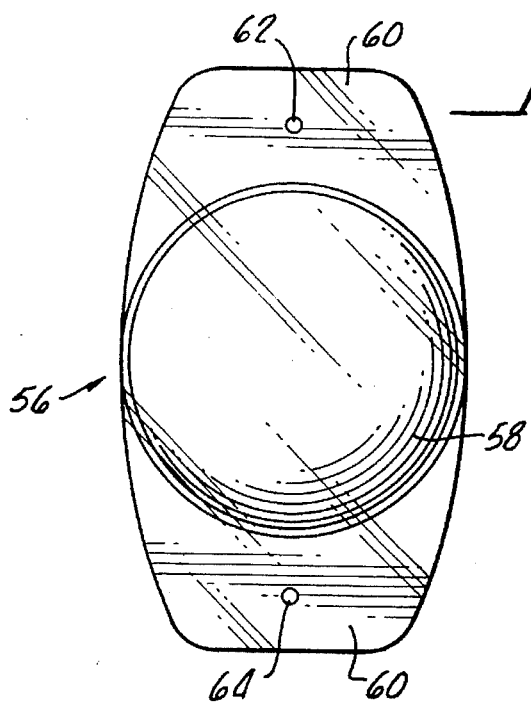
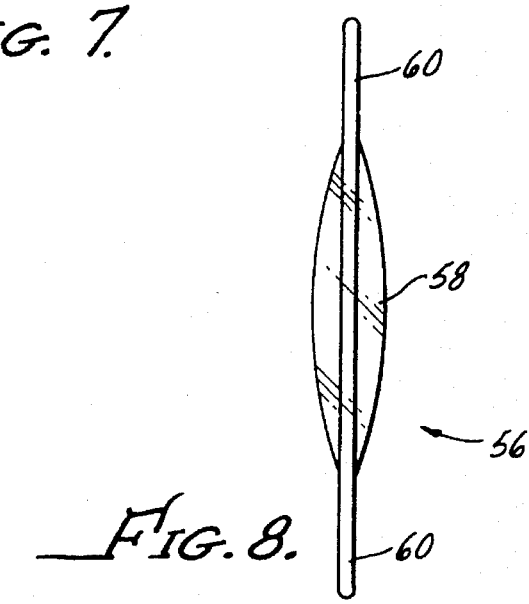
FIG. 7.
FIG. 8.
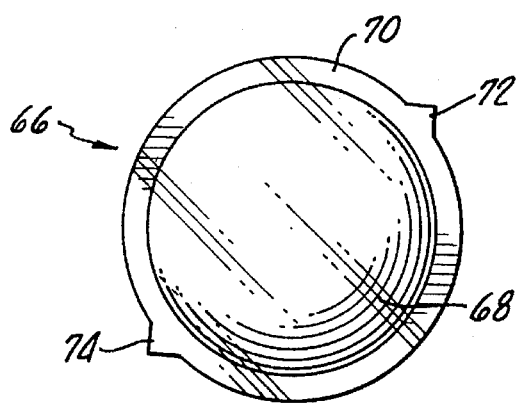
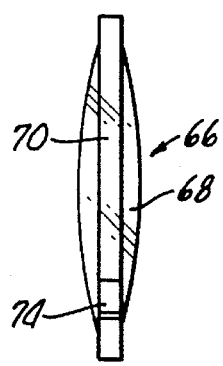
FIG. 9.
FIG. 10.

CAST MOLDING OF INTRAOCULAR LENSES

BACKGROUND OF THE INVENTION

This invention relates to an improved mold assembly for fabricating intraocular lenses. More particularly, the invention relates to disposable lens molds having novel features which permit easy alignment of the two mold halves and ensure properly finished lens edges by minimizing flash.

The use of intraocular lenses (IOLs) to improve vision and/or to replace damaged or diseased natural lenses impaired by cataracts, has obtained wide acceptance for a long period of time. Accordingly, a variety of IOLs have been developed for surgical implantation into the posterior or anterior chambers of the eye according to a patient's needs. Known IOLs comprise an optical lens portion or optic which includes an optical zone, and one or more supporting structures, called fixation members or haptics, for contacting eye tissue to fix or hold the IOL in the proper position after implantation. The optic may comprise a relatively hard or rigid material such as, for example, polymethylmethacrylate (PMMA), or, increasingly, a soft, resilient polymeric material, such as silicone or an acrylic material. The softer optic materials are advantageous in that they are deformable, e.g. foldable, so that for implantation a smaller incision may be surgically cut in the eye than for implantation of "hard" intraocular lenses.

It is known in the prior art that intraocular lenses made from soft biocompatible materials such as silicone polymers or acrylics possess desirable properties, having sufficient structural integrity, elasticity, and a small enough size to permit them to be folded for insertion through a small incision. After insertion, the soft lens is resilient enough to regain its original molded shape.

To fabricate a soft, biocompatible lens using prior art molding techniques, a polished stainless steel mold, having a mold cavity in the shape required for the correct refraction of light for the material selected, is employed. In the case of silicone, the uncured silicone polymer is introduced into the mold cavity, in an amount dictated by considerations relating to the lens size, refractive power, and structure, and allowed to cure. Several methods of molding the lens have been employed, including injection molding, liquid injection molding, compression molding, and transfer molding.

there are several significant problems associated with the above described lens molding techniques, particularly involving the employment of re-usable steel molds to fabricate the lenses. One problem is that the process is labor intensive. The silicone elastomer used to mold the lens leaves a residue in the mold, requiring cleaning of the mold between each molding cycle. Besides being labor intensive, the cleaning step results in a lot of downtime for the equipment, further increasing production costs. Another problem is that of frequent tool damage and wear because of the repeated cleanings, resulting in the need to often replace the molds, which again drives up costs and increases downtime of the equipment.

Another problem with using steel molds is one of quality control with respect to the molded lens. In contrast to contact lenses, it is imperative that an IOL have a smooth, polished edge, because of its location within a patient's eye. Improperly finished lens edges of such IOL's may result in damage to the interior structures of the eye, particularly abrasions of the iris surface and tearing of the trabecular meshwork. Unfortunately, steel, which is relatively non-compliant, typically leaves minute gaps between mold halves when they are clamped during the molding operation, due to construction tolerances. Consequently, molding material leaks out through the gaps during molding, resulting in a phenomenon known as "flash", which is unwanted attached material at the parting line (between the mold halves) on the molded lens. This flash material must be ground off and the lens edges polished in a labor intensive subsequent finishing step, again increasing production costs.

What is needed, therefore, is a new IOL mold which is inexpensive, less labor intensive, and produces a high quality IOL having smooth edges which minimizes postmolding finishing.

SUMMARY OF THE INVENTION

This invention solves the problems outlined above by providing a disposable plastic mold assembly for an IOL or the optic body thereof which is inexpensive, less labor intensive, and produces an optic body or IOL having smooth edges which require little or no post-mold finishing work Numerous innovative features of the invention include an edge design which assures a seal between the male and female molds to thereby prevent flash during the cast molding operation, and the provision of a means for axially pre-aligning the male and female molds during assembly, consisting of an interference fitting relationship between the male and female molds. An additional feature is a means for maintaining contact between the male and female molds during casting, which particularly involves the provision of a negative draft angle on the inner surface of the female mold's outer wall, or, alternatively, texturing which is applied to that inner surface so that it engages the outer edge at the top of the male mold during assembly. Finally, yet another important feature of the invention is a means for improving axial and, optionally, rotational orientation to produce lens edge geometries without unwanted steps on the lens edge. The alignment is achieved with interlocking steps on the male and female molds. The interlocking elements may be pins or annular elements.

More specifically, the disposable plastic mold assembly comprises a male mold portion having a first molding surface and a female mold portion having a second molding surface and being sized to receive the male mold portion. The assembly is constructed so that when the male mold portion is fully received by the female mold portion, the first and second molding surfaces are engaged to create a lens mold cavity. Importantly, as discussed above, the female mold portion is relatively shaped to receive the male mold portion axially in an interference fitting relationship, for substantially axially pre-aligning the male and female mold portions together.

Preferably, both the male and female mold portions are generally cylindrical, and each comprise a generally cylindrical sidewall, with the first molding surface being oriented exteriorly to the space bounded by the sidewall of the male mold portion and the second molding surface being oriented interiorly to the space bounded by the sidewall of the female mold portion. Therefore, as the male mold portion is received axially within the space bounded by the sidewall of the female mold portion to assemble the mold, it is the respective sidewalls of the male and female mold portion which are in interfering contact to create the interference fitting relationship.

An important feature of the invention is that the sidewall of the female mold portion is oriented at a negative draft angle, so that after the male mold portion has been received by the female mold portion, the negative draft angle inhibits the male mold portion from backing away therefrom; i.e. out of the space bounded by the sidewall of the female mold portion.

Another important feature of the invention is that the first and second molding surfaces include surface features which are relatively shaped to interlock to further provide axial and rotational alignment of the male and female mold portions, as the male mold portion is received into the female mold portion to form the mold assembly. Preferably, the first molding surface includes at least one recess and the second molding surface includes at least one corresponding projection, wherein the projection and recess are adapted to interlock to provide the aforementioned axial and rotational alignment. In the preferred embodiment, the opening comprises an annular groove, and the projection actually comprises a plurality of projections, each of which spans an arc of about 30 degrees about the azimuth of the second molding surface and is adapted to be received into the annular groove. Both the recess and the projections are stepped so that they each include a sloped surface and a flat surface. The respective stepped surfaces of each of the recess and the projections are adapted to correspond and mate with one another to axially align the two mold portions.

In order to minimize flash and therefore mold a smooth edge free of discontinuities, the male and female mold portions each include an annular sealing surface which circumscribes the lens mold cavity. The sealing surfaces are adapted to contact one another to seal the outer edges of the lens mold cavity when the first and second molding surfaces are fully engaged, thereby preventing the leakage of lens molding material from the lens molding cavity. An inventive feature is that one of the sealing surfaces is oriented at an acute angle with respect to the other sealing surface, so that the two sealing surfaces will contact generally along a single annular line, thereby providing a more positive lens mold cavity edge seal.

It should be noted that in some circumstances, it may be advantageous to retain the IOL or the optic body for an IOL in the lens mold cavity after completing the molding process. This permits the option to transport the molds to a different location for demolding and, in the case of molding an optic body, to complete the IOL assembly. Such an option may be advantageous if the second location has a greater labor pool having appropriate skills, or lower labor rates.

In another aspect of the invention, a disposable plastic mold assembly for cast molding an intraocular lens or the optic body thereof comprises a male molding portion having a first molding surface and a female mold portion having a second molding surface and being shaped to receive the male mold portion. When the male mold portion is fully received by the female mold portion, the first and second molding surfaces are engaged to create a lens mold cavity. Importantly, each of the first and second molding surfaces include surface features which are shaped to mate together to provide axial alignment of the male and female mold portions.

Another feature of the invention is that an annular lens molding material overflow reservoir has been molded into the respective first and second molding surfaces, radially outwardly of the interlocking surface features. The overflow reservoir receives excess lens molding material which is squeezed out of the lens molding cavity as the two mold portions approach one another, and before the mold cavity is sealed. The excess material is supplied to the cavity initially in order to prevent the formation of bubbles in the lens during the cast molding process.

In yet another aspect of the invention, a disposable plastic mold assembly for cast molding an intraocular lens or optic body thereof comprises a male molding portion having a first molding region and a female mold portion having a second molding region and being adapted to receive the male mold portion. When the male mold portion is fully received by the female mold portion, the first and second molding regions are engaged to create a lens mold cavity for receiving a predetermined quantity of lens molding material. Each of the male and female mold portions include an annular sealing surface which circumscribes the lens mold cavity. The sealing surfaces are adapted to contact one another to seal the outer edges of the lens mold cavity when the first and second molding regions are fully engaged, so as to prevent the leakage of lens molding material from the lens molding cavity. Significantly, one of the sealing surfaces is oriented at an acute angle with respect to the other sealing surface, so that the two sealing surfaces will form a line contact over the entire circumference of the lens, thereby providing a more positive lens mold cavity edge seal.

The invention together with additional features and advantages thereof may best be understood by reference to the following description taken in conjunction with the accompanying illustrative drawing.

BRIEF DESCRIPTION OF THE DRAWING

FIG. 7 is a top plan view of a plate IOL, which may be molded in accordance with the teachings of the invention;

FIG. 8 is a side view of the plate IOL illustrated in FIG. 7;

FIG. 9 is a top plan view of one embodiment of an IOL optic body, which may be molded in accordance with the teachings of the invention; and FIG. 10 is a side view of the optic body illustrated in FIG. 9.

DETAILED DESCRIPTION OF THE PREFERRED EMBODIMENT

Figure 1:
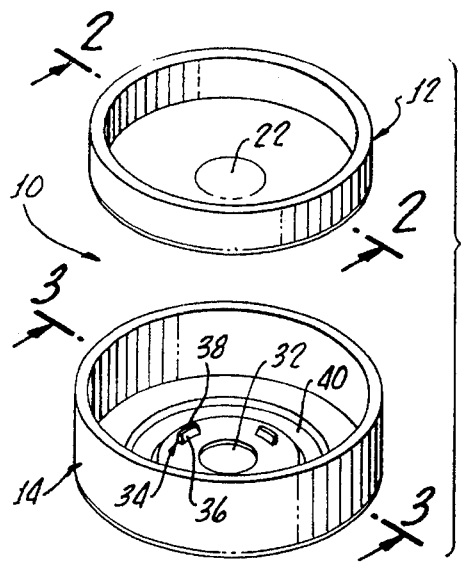
FIG. 1 is an exploded view in perspective, showing male and female disposable mold halves for molding the optic body of an IOL, constructed in accordance with the teachings of the invention.
Figure 5:
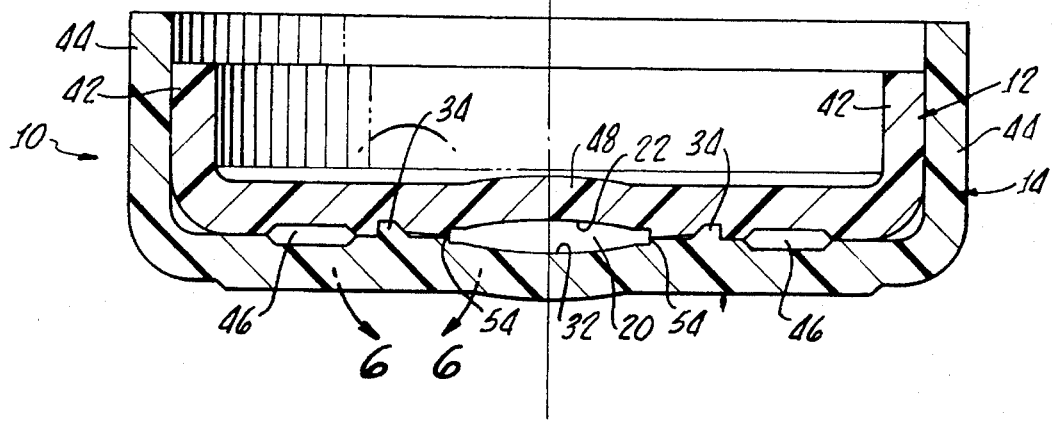
FIG. 5 is a cross-sectional view illustrating the male and female mold halves shown in FIG. 1 in their assembled position, in preparation for molding an intraocular lens.

Referring again to the drawing, there is shown generally at 10 in FIGS. 1 and 5, a mold for an IOL optic or optic body which is fabricated in accordance with the present invention. The mold 10 comprises a male mold hall 12 which is insertable into a female mold half 14 (FIGS. 1, 2, 3 and 5). Each mold half 12, 14 is preferably cylindrical, having a cylindrical wall, an open end, and a closed end. The male mold half 12 has an exterior molding surface 16 on its closed end, while the female mold half 14 has a complementary interior molding surface 18 on its closed end. To create a mold cavity 20 (FIG. 5) for the IOL optic body, the male mold half 12 is adapted to be inserted axially along the axis 21 into the female mold half 14, in a manner shown best in FIG. 5. When the male mold is fully received within the female mold, the respective complementary molding surfaces 16 and 18 (see FIGS. 2 and 3, respectively) of the male and female mold halves 12, 14 come into contacting relationship with one another to form the mold cavity 20, as well as various other advantageous features, as will be discussed more fully hereinbelow.

Figure 2:
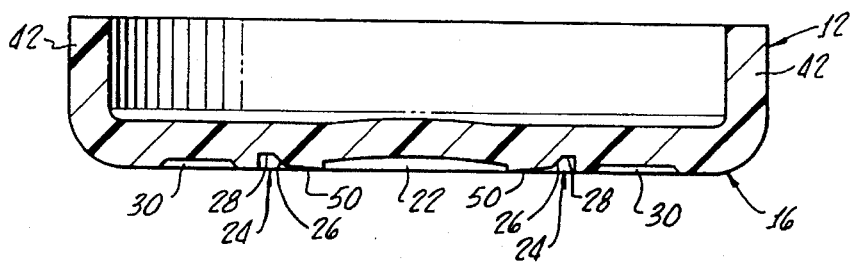
FIG. 2 is a cross-sectional view of the male mold half, taken along lines 2—2 of FIG. 1.
Figure 6:
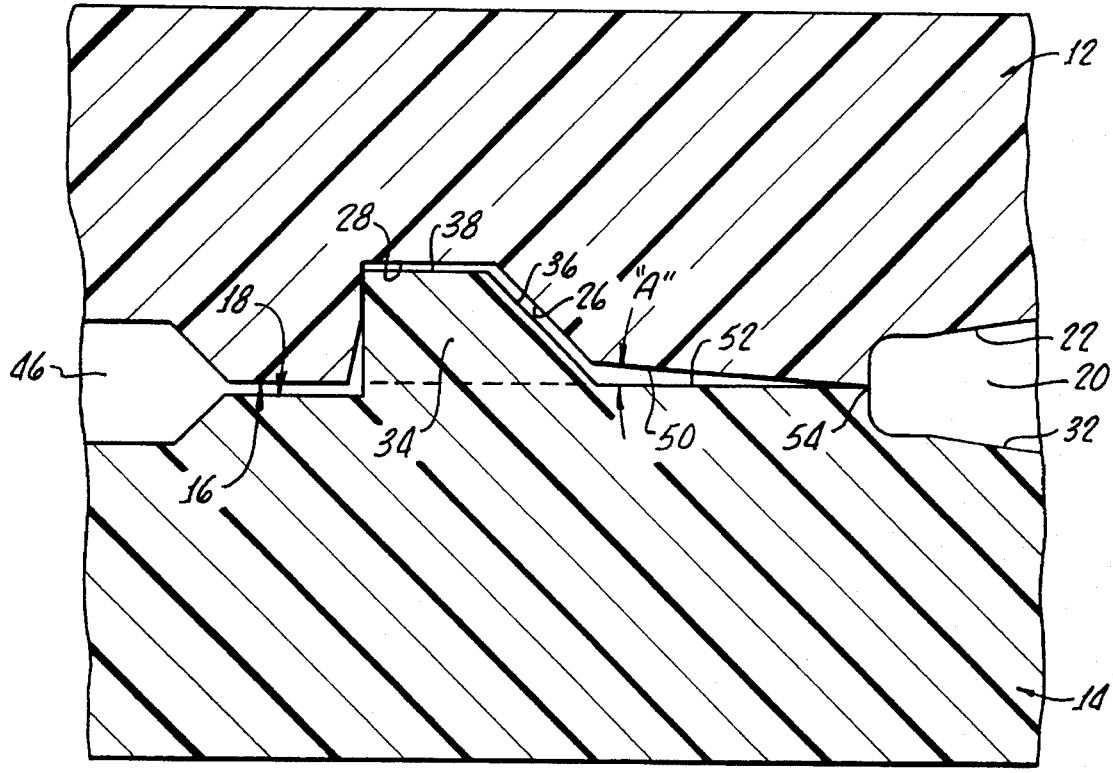
FIG. 6 is an enlarged cross-sectional view of the area delineated by the arc 6—6 in FIG. 5.

Now referring particularly to FIG. 2, it can be seen that the male mold half 12 includes, on its exterior molding surface 16, a first generally circular molding recess 22, which is located at substantially the radial center of the molding surface. The recess 22 may be of various depths and radii, depending upon the desired size and diopter strength of the IOL optic body to be fabricated. Radially outwardly of the recess 22 is a stepped annular groove 24, which comprises a sloped surface 26 and a bottom surface 28 (FIGS. 2 and 6). Radially outwardly of the groove 24 is a first annular overflow reservoir recess 30, which may be of any desired width and depth, in accordance with the expected quantity of overflow lens molding material (preferably a silicone monomer) for a particular molding operation, as will be more fully explained hereinbelow.

Figure 4:
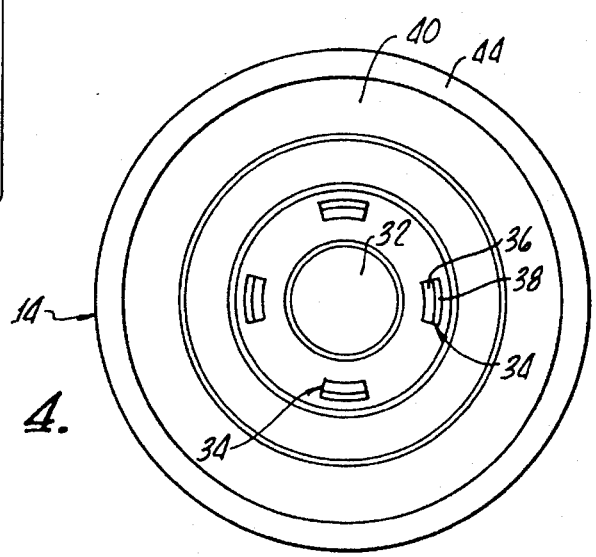
FIG. 4 is a top plan view of the female mold half illustrated in FIG. 1.
Figure 3:
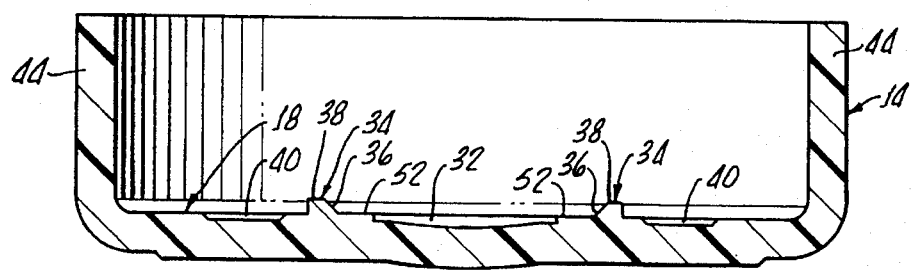
FIG. 3 is a cross-sectional view of the female mold half, taken along lines 3—3 of FIG. 1.

Now with reference to FIGS. 3 and 4, particular features of the female mold half 14 are illustrated. At its radial center is located a second generally circular molding recess 32, which is sized and adapted to correspond with the first molding recess 22 in the male mold half 12. Radially outwardly of the molding recess 32 are a plurality of stepped projections 34, which each include a sloped surface 36 and top surface 38. In the preferred embodiment, there are four projections 34 arranged in equally spaced fashion about the circumference of the mold half 14, with each projection spanning an arc of about 30 degrees. The projections 34 are sized and arranged to mate with the stepped groove 24 in the male mold half 12, and their arrangement is shown most clearly in FIG. 4. The groove may be continuous or discontinuous. A discontinuous groove could be used to provide rotational orientation.

As in the case of the male mold half 12, radially outwardly of the projections 34 is a second annular overflow reservoir recess 40, which is sized and adapted to correspond with the first overflow reservoir recess 30.

Both of the male and female mold halves 12 and 14, respectively, are preferably fabricated of relatively rigid injection molded plastic, preferably optical grade polycarbonate, which has a high melt flow index and can therefore be molded with a high degree of precision. Other materials may be used as well, such as polyolefin, polypropylene, and polystyrene. Typically, the cure cycle for the injection molded mold halves will be about 10 to 40 seconds at 60 to 80 degrees C.

There are a number of advantages to using plastic mold halves rather than the prior art steel molds. First, they are disposable, so there is no need to engage in the labor intensive practice of cleaning the lens molds between each production run. It is true that the molds used to make the plastic lens mold halves will have to be cleaned periodically, since injection moldable thermoplastics like those used to make the lens mold halves leave residue, but the molds need only be cleaned every few hours, permitting the manufacture of many plastic lens molds between scheduled downtimes. Second, the plastic mold halves can easily be molded to include a number of surface features which improve the quality of the finished lens, as have been discussed previously. Third merely by changing the optic pins in the mold for producing the lens molds, it is possible to produce different lens molds for each dioptric power, which then may be provided with an etched dioptric identification marking (e.g. using a laser etching device) and stored for later use in molding a lens requiring that particular dioptric power. Yet another advantage is that the use of cheap, disposable plastic molds permits the simultaneous curing of lenses in numerous molds.

Referring now particularly to FIGS. 5 and 6, the process for assembling the mold halves 12 and 14 to mold an IOL optic body will now be described. To assemble the mold 10, the male mold half 12 is inserted axially downwardly into the female mold half 14, as shown. In order to achieve axial pre-alignment of the two mold halves, so that the various surface features of each molding surface 16 and 18, respectively, will correspond as intended, the circumferential sidewall 42 of the male mold 12 is preferably adapted to be in an interference fitting relationship with the circumferential sidewall 44 of the female mold 14 when the male mold 12 is inserted axially into the female mold 14. This interference fit relationship has been found to provide axial pre-alignment of the two mold halves 12, 14 to within about 0.0005 to 0.002 inches. Additionally, in order to prevent the male mold 12 from backing out of the female mold 14, thereby maintaining contact between the male and female molding surfaces during casting, it is preferred that the sidewall 44 of the female mold 14 have a negative draft angle orientation of about 0–2 degrees (preferably 0.5 degrees) with respect to the vertical; i.e. the diameter of the sidewall 44 decreases and the interference fit between the sidewalls 42 and 44 consequently becomes more pronounced, as the respective open ends of the mold halves are approached. Optionally, the sidewall 42 of the male mold half 12 additionally has a positive draft angle orientation, which further increases the security of the assembled mold 10. If desired, as an alternative to or in addition to the above described negative draft angle for preventing the backing away of the male mold half from the female mold half, a rib, textured surface, or the like may be molded onto the contacting surface of either the male or female mold sidewall.

As noted above, when the respective molding surfaces 16 and 18 are in interference contact, the first and second molding recesses 22 and 32, respectively, together form the optic body mold cavity 20. The two annular overflow reservoir recesses 30 and 40 together form an annular overflow reservoir 46. Additionally, the stepped projections 34 of the female mold half 14 are adapted to be interlocked with the stepped annular groove 24 in the male mold half 12, thereby providing an additional axial index for fine tuning the alignment of the two mold halves, while also aligning the two molding surfaces 16 and 18 radially. This feature helps to produce desired lens edge geometries without unwanted finishing steps on the lens edge, and also to minimize optical prism. It should be noted, however, that various other such alignment features could also be employed. For example, a different number than four projections 34 could be employed, each projection could span an arc greater than or less than 30 degrees, a single annular projection could be employed, or the groove 24 might not be continuous. If it were not continuous, the corresponding grooves 24 and projections 34 would provide a rotational index as well as an axial one, preventing relative rotation of the two mold halves and helping to ensure a specific mold orientation. Alternatively, the interlocking projections and grooves could be fabricated as pins and corresponding holes, which also would provide both an axial and a rotational index.

When it is desired to mold an optic body, a predetermined quantity of lens molding material (e.g. silicone polymer or monomer), preferably about 4 to 5 times the quantity required for the lens, is dispensed into the second molding recess 32 in the female mold 14. The male mold half 12 is then inserted into the female mold half 14. A device (not shown) for applying a varying axial clamping force (ranging from about 0 to 40 or 50 lb), e.g. a spring biased plunger, may be employed to apply such a force against the interior surface 48 of the male mold half 12 (FIG. 5), but only beyond the edge of the lens forming cavity in order not to damage the optic body. As the molding surface 16 of the male mold 12 approaches the molding surface 18 of the female mold, the excess monomer exits the lens cavity 20, flowing past the groove 24 and projections 34 and into the annular overflow reservoir 46. This process, wherein excess monomer is dispensed and then "squeezed out" into the overflow reservoir, assists in preventing bubbles from forming in the lenses. Finally, the two molding surfaces contact sufficiently to seal the lens cavity 20, thereby preventing further outflow of monomer therefrom.

Yet another advantageous feature of the invention is a unique edge design which assures such an effective seal between the male and female molds that flash is substantially prevented during the casting operation. As best seen in FIGS. 2, 3, and 6, the exterior molding surface 16 of the male mold half 12 includes an annular angled sealing surface region 50 located radially outwardly of and adjacent to each end of the first molding recess 22. The angle A (FIG. 6) is preferably a very shallow one (about 1–4 degrees in the preferred embodiment). The interior molding surface 18 of the female mold half 14 includes a preferably flat annular sealing surface region 52 located radially outwardly of and adjacent to each end of the second molding recess 24, and in corresponding relationship to the angled sealing surface 50. Therefore, when the two molding surfaces 16 and 18 contact each other to seal the lens cavity 20, the contact occurs along a single annular line or circle 54 around the cavity 20, as illustrated in FIGS. 5 and 6, because of the angled orientation of the sealing surface region 50, rather than along the entire widths of the respective sealing surface regions 50, 52, as would be the case if both surfaces were flat. This single line contact results in a positive and more effective sealing of the mold cavity 20, because the entire force applied against the interior surface 48 of the male mold half 12 by the clamping device is applied along that single line, rather than across the entire radial width of the sealing surfaces. It would, of course, be within the scope of the invention to angle the sealing surface 52, rather than 50, if desired.

Once the two molding surfaces 16 and 18 are fully engaged, and the mold cavity 20 has been sealed about its edges, the silicone monomer lens material is heated in a known fashion to about 60–80 degrees C, and maintained for a cure cycle sufficient to ensure cross-linking of the silicone polymer, typically ranging between 30 minutes and 3 hours, as is well known in the art.

While the disclosed preferred embodiment is particularly adapted for molding an IOL optic body, the inventive mold assembly may also be used to mold an entire IOL. Various types of IOL's are in use today. For example, a plate IOL or lens 56 is depicted in FIGS. 7 and 8, which includes an optic body 58 and a plate region 60. Typically, plate lenses are generally solid one-piece lenses, which sometimes include holes 62, 64 which may be used by a surgeon to move the lens during a procedure. The mold assembly 10 may be modified to mold such a lens in its entirety, as well as other non-circular shapes, and IOL's comprising a plurality of pieces. Using the principles of the invention, one or more holes or openings (like holes 62, 64) may be molded into the lens for mechanical or physiological reasons.

As discussed in the Background of the Invention, it is also well known in the art to utilize formation members, or haptics, for contacting eye tissue to fix or hold an IOL optic body in proper position after implantation. It is within the scope of the invention, and the purview of one of ordinary skill in the art, to insert mold the haptics as part of the lens molding process. Alternatively, a pair of buttresses may be molded onto opposing edges of the lens to provide lens attachment points for the haptics, as shown in FIGS. 9 and 10. Loops may be placed in the disposable molds prior to lens material dispensing and curing. In this case, the loops are said to be insert molded. Such and IOL optic body 66 is illustrated in FIGS. 9 and 10, by way of example. The optic body 66 comprises part of a three-piece IOL, known in the art, which includes an optic region 68, surrounded by a spare tire region 70. The spare tire region 70 includes buttresses 72 and 74, to which the haptics may be attached. If buttresses are utilized, it may be necessary, for tooling reasons, to dispense with the feature of angling one of the sealing surfaces 50 and 52, and maintain both of them as substantially flat surfaces. While this might diminish the quality of the seal to some extent, the seal would still be adequate, particularly since the two mold halves 12 and 14 are fabricated of plastic, rather than steel. Since plastic is a more compliant material, it does not tend to leave gaps when clamped, as steel may.

After the process of molding the IOL or IOL optic body is complete, it is demolded and the mold assembly is discarded. This step may be performed immediately after molding, or, alternatively, the molds may be packaged and shipped to another location with the molded IOL or optic body still inside, where the demolding step can then take place and the IOL's themselves can subsequently be assembled (if further assembly is required; i.e. attachment of the spare tire region and insertion of the haptics). Such an approach may be advantageous if the second location has a more suitable labor force or if labor costs are significantly lower. Yet another alternative is to use the still-assembled mold assembly containing the lens as a fitted lens holder during subsequent production steps, such as haptic attachment.

Accordingly, although an exemplary embodiment of the invention has been shown and described, many changes, modifications, and substitutions may be made by one having ordinary skill in the art without departing from the spirit and scope of the invention, as defined in the claims appended hereto.

What is claimed is:

1. A disposable plastic mold assembly, comprising:
   a generally cylindrical male mold portion having a first substantially planar molding surface and a sidewall, said first molding surface being oriented exteriorly to space bounded by the first molding surface and the sidewall;
   a generally cylindrical female mold portion having a second substantially planar molding surface and a sidewall, said female mold portion being adapted and sized to receive said male mold portion and the second molding surface being oriented interiorly to space bounded by the second molding surface and the sidewall of the female mold portion, such that when the male mold portion is fully received by the female mold portion, said first and second molding surfaces engage each other substantially along a single plane of contact to create a mold cavity;

the male and female mold portions being relatively shaped so that the female mold portion receives the male mold portion axially in an interference fitting relationship for substantially axially pre-aligning the male and female mold portions together, the respective sidewalls of each of the male and female mold portions being in interfering contact as the male mold portion is received within the space bounded by the sidewall of the female mold portion to create said interference fitting relationship;

wherein the sidewall of said female mold is oriented at a negative draft angle, so that after said male mold portion has been received by said female mold portion, said negative draft angle inhibits the male mold portion from backing away therefrom.

2. A disposable plastic mold assembly as recited in claim 1, wherein said negative draft angle is less than about 2 degrees.

3. A disposable plastic mold assembly as recited in claim 2, wherein the sidewall of said male mold portion is oriented at a positive draft angle.

4. A disposable plastic mold assembly as recited in claim 1, wherein said first and second molding surfaces include surface features which are relatively shaped to interlock to provide further axial alignment of the male and female mold portions as the male mold portion is received into the female mold portion to form said mold assembly.

5. A disposable plastic mold assembly as recited in claim 4, wherein said surface features are further relatively shaped to interlock to provide rotational alignment of the male and female mold portions as the male mold portion is received into the female mold portion to form said mold assembly.

6. A disposable plastic mold assembly as recited in claim 4, wherein said first molding surface includes at least one recess and said second molding surface includes at least one corresponding projection, said at least one projection and said at least one recess being adapted to interlock to provide said further axial alignment.

7. A disposable plastic mold assembly as recited in claim 6, wherein said at least one recess comprises an annular groove, and said at least one projection comprises a plurality of projections, each said projection spanning an arc of about 30 degrees about the azimuth of said second molding surface and being adapted to be received into said annular groove.

8. A disposable plastic mold assembly as recited in claim 6, wherein said at least one recess and said at least one projection are each stepped such that they include a sloped surface and a flat surface, the respective stepped surfaces of each of the at least one recess and the at least one projection being adapted to correspond and mate with one another.

9. A disposable plastic mold assembly as recited in claim 1, wherein said male and female mold portions each include a sealing surface which circumscribes said mold cavity, the sealing surfaces being adapted to contact one another to seal the outer edge of the mold cavity when the first and second molding surfaces are fully engaged, thereby preventing the leakage of lens molding material from said mold cavity, wherein one of said sealing surfaces is oriented at an acute angle with respect to the other sealing surface, so that the two sealing surfaces are adapted to contact along a single line, the outer edge of the mold cavity being in substantially the same plane as the radial center of the mold cavity.

10. A disposable plastic mold assembly as recited in claim 1, wherein said mold cavity contains an optic body from an intraocular lens, said optic body having two convex optical surfaces.

11. A disposable plastic mold assembly as recited in claim 1, wherein said mold cavity contains an intraocular lens, said intraocular lens having two convex optical surfaces.

12. A disposable plastic mold assembly as recited in claim 5, wherein an annular lens molding material overflow reservoir is located radially outwardly of said interlocking surface features.

13. A disposable plastic mold assembly as recited in claim 9, wherein said one sealing surface is oriented at an angle of about 1–4 degrees with respect to the other sealing surface.

14. A disposable plastic mold assembly as recited in claim 1, said mold assembly being selectively shaped to mold an optic body having a predetermined dioptric power, and having identification markings thereon to indicate said dioptric power, said mold assembly further being adapted to be inventoried with other similar mold assemblies which are adapted to mold optic bodies having other dioptric powers.

15. A disposable plastic mold assembly as recited in claim 1, wherein both the male and female mold portions are molded of a thermoplastic material.

16. A disposable plastic mold assembly as recited in claim 15, wherein said thermoplastic material is a polycarbonate.

17. A disposable plastic mold assembly as recited in claim 10, wherein said optic body comprises a silicone-based polymer.

18. A disposable plastic mold assembly as recited in claim 10, wherein the optic body has two convex optical surfaces.

* * * * *